United States Patent
Chang et al.

(10) Patent No.: US 7,122,008 B2
(45) Date of Patent: Oct. 17, 2006

(54) BLOOD PRESSURE DIAGNOSTIC AID

(75) Inventors: David B. Chang, Tustin, CA (US); James E. Drummond, Lincoln City, OR (US); Jane F. Emerson, Irvine, CA (US)

(73) Assignee: Magnetus LLC, Irvine, CA (US)

( * ) Notice: Subject to any disclaimer, the term of this patent is extended or adjusted under 35 U.S.C. 154(b) by 210 days.

(21) Appl. No.: 10/934,843

(22) Filed: Sep. 3, 2004

(65) Prior Publication Data

US 2006/0052711 A1    Mar. 9, 2006

(51) Int. Cl.
*A61B 5/02* (2006.01)

(52) U.S. Cl. .................. 600/485; 600/490; 600/500

(58) Field of Classification Search .............. None
See application file for complete search history.

(56) References Cited

U.S. PATENT DOCUMENTS 5,497,778 A * 3/1996 Hon ........................ 600/485

2002/0188206 A1* 12/2002 Davis et al. ............. 600/485

* cited by examiner

*Primary Examiner*—Robert L Nasser
(74) *Attorney, Agent, or Firm*—MacPherson Kwok Chen & Heid LLP; Tom Chen

(57) ABSTRACT

A medical diagnostic method using systolic and diastolic blood pressures, and pulse frequency of a patient is provided to compute a normalized diastolic distensibility value and a normalized peripheral resistance value, and to automatically compute the product of the normalized diastolic distensibility value and the normalized peripheral resistance value to generate a first product value. The first product value is compared to a stored distribution of normalized diastolic distensibility and a normalized peripheral resistance values for comparable individuals to determine if the first product value is equivalent to a value determined to indicate an abnormal condition. Particular values of the computed parameters aid in determining the etiology of hypertension and direct selection of pharmacotherapy.

24 Claims, 9 Drawing Sheets

Correlation of D with R: D = mR+b  m = -1

BLOOD PRESSURE DIAGNOSTIC AID

BACKGROUND

1. Field of the Invention

The present invention relates to medical diagnostic equipment, and more particularly to medical diagnostic equipment related to the measurement and interpretation of blood pressures.

2. Description of the Related Art

The effects of high blood pressure continues to be a serious health problem. In the early 1990's, it was reported that two-thirds of Americans die with atherosclerotic blood vessels and that one-half of all Americans die as a result of these lesions.

There are many possible causes of high blood pressure each relating to different physiological mechanisms. In response, different hypertensive pharmaceuticals have been developed, each targeting one or more of the potential mechanisms. Examples are calcium channel blockers, angiotensin-converting enzyme inhibitors, beta-blocking drugs and their hybrids, diuretics, centrally-acting alpha$_2$ agonists, alpha$_1$-blocking agents, vasodilators, and adrenergic-blocking agents. Some of these medications act primarily on the microvascular (peripheral) resistance to blood flow, others on the lowered distensibility of larger arteries, cardiac output, or on various combinations of these.

Medical doctors and other practitioners routinely determine systolic and diastolic blood pressures using an inflatable cuff and sphygmomanometer and measure heart rate by manual timing of the pulse. Possible disease states are inferred from these values and this may lead to the use of additional diagnostic tests. The additional tests, such as measurement of cardiac output, for example, are often more invasive, time-consuming, and expensive. For these reasons, practitioners may prescribe medicines without performing them. This less-than-optimal therapy increases the likelihood of adverse side effects and when more than one agent is involved, increases the potential for undesirable drug interaction.

Clearly, in deciding on which type of hypertensive medication to prescribe for a particular patient, it is desirable to identify the underlying causes so that an informed decision, based on an accurate and timely diagnosis, can be made.

SUMMARY

The present invention provides a method and associated apparatus, which combine measures of systolic and diastolic blood pressure and pulse frequency (heart rate), producing quantitative data on normalized diastolic distensibility, normalized peripheral resistance, and a parameter based on these which is independent of cardiac output. These results can be compared with normal and abnormal results from recorded empirical data.

In one aspect of the present invention, the method can include measuring, with standard or automatic equipment, the systolic and diastolic blood pressures, and pulse frequency (heart rate) of a patient; entering, electronically or with a keyboard, the data into a preprogrammed computer; reading from the computer display, normalized diastolic distensibility and normalized peripheral resistance, the product of theses two quantities, and the relation of these quantities to stored normal or abnormal distributions of such quantities for comparable individuals plus a list of medications that are indicated in those abnormal conditions.

In another aspect of the present invention, a medical diagnostic method using systolic and diastolic blood pressures, and pulse frequency of a patient is provided to compute a normalized diastolic distensibility value and a normalized peripheral resistance value, and to compute the product of the normalized diastolic distensibility value and the normalized peripheral resistance value to generate a first product value. The first product value is compared to a stored distribution of normalized diastolic distensibility and normalized peripheral resistance values for comparable individuals to determine if the first product value is equivalent to a value determined to indicate an abnormal condition.

The field of the present invention relates to measuring and interpreting blood pressures, bp, and pulse rate, f, in terms of hardening of the arterioles vs. peripheral resistance to blood flow. The venue for these actions can be a medical practitioner's office or any inpatient or outpatient location. The present method departs from current procedures by measuring blood pressure and pulse rate and deducing normalized values of arterial distensibility and peripheral resistance without using a transesophageal transducer or catheter insertion in a blood vessel.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE FIGURES

Embodiments of the present invention and their advantages are best understood by referring to the detailed description that follows. It should be appreciated that like reference numerals are used to identify like elements illustrated in one or more of the figures.

DETAILED DESCRIPTION

Figure 2:
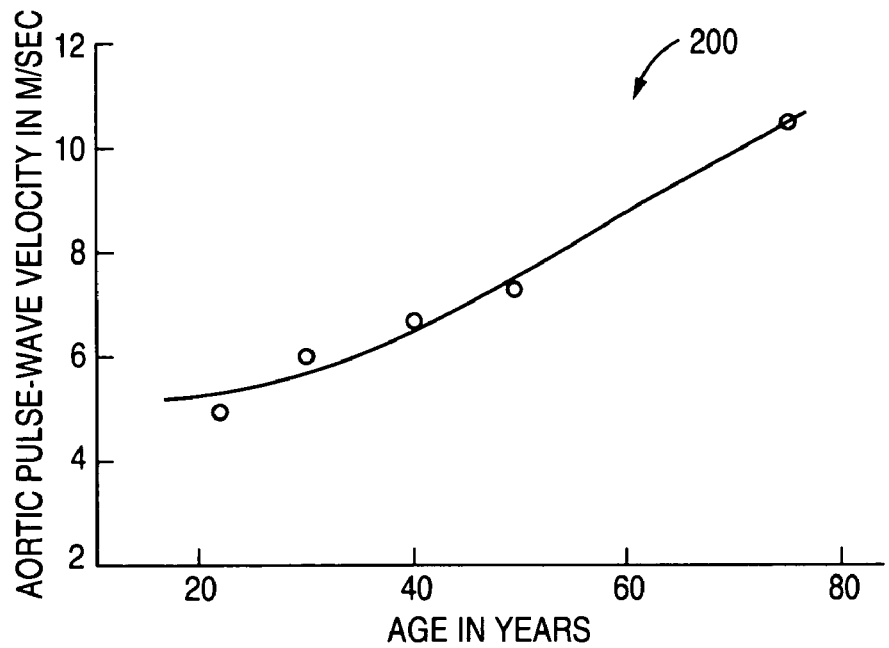
FIG. 2 is a plot of average aortic pulse wave velocity vs. age.

At each ventricular ejection contraction, a volume of blood, the stroke volume is injected into the aorta. The aorta stretches to accommodate the stroke volume and an accompanying pressure pulse launches down the aorta into the main arteries. FIG. 2 shows a plot 200 of the velocity of a pulse along the major arteries as a function of the age of an individual. The pulse can travel at speeds of between about 5–10 meters/sec—the lower speeds typically applying at lower ages and the higher speeds applying at higher ages. Since a typical pulse rate is of the order of one pulse per second, the high pulse velocity indicates that to a first approximation, the entire arterial tree feels the same pressure practically simultaneously.

Figure 3:
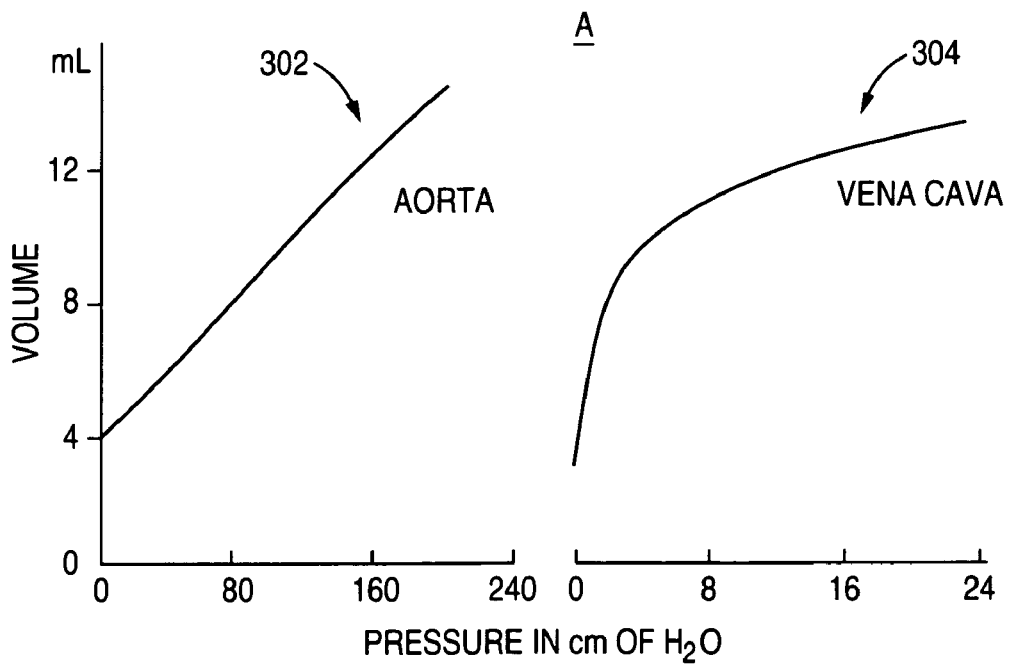
FIG. 3 shows volume vs. pressure plots for human aorta and vena cava.

The pressure in the arterial tree is related to the distension of the arteries. As shown in FIG. 3, over a wide range of pressures, the plot 302 of the relation between the blood volume (distension) and the pressure is linear as contrasted with the plot 304 representing low-pressure veins. Accordingly:

$$\delta V_i = D_i \delta P \quad [1]$$

where $\delta V_i$ denotes the change in volume in the $i^{th}$ artery due to a pressure change $\delta P$, and $D_i$ denotes the distensibility of the $i^{th}$ artery.

The pressure in the arterial tree does not remain elevated after injection of a stroke volume of blood, because the pressure drives the blood from the arterial tree into the microvasculature.

Figure 4:
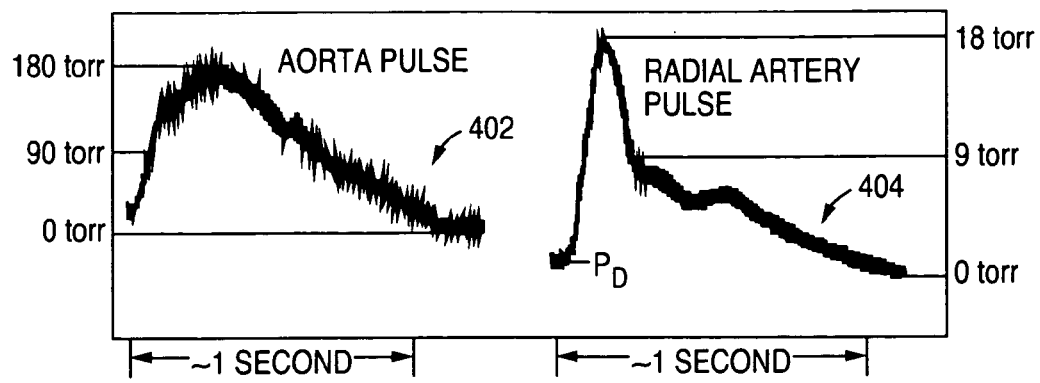
FIG. 4 shows distortion over time of the arterial pressure pulse from the aortal pulse.
Figure 5:
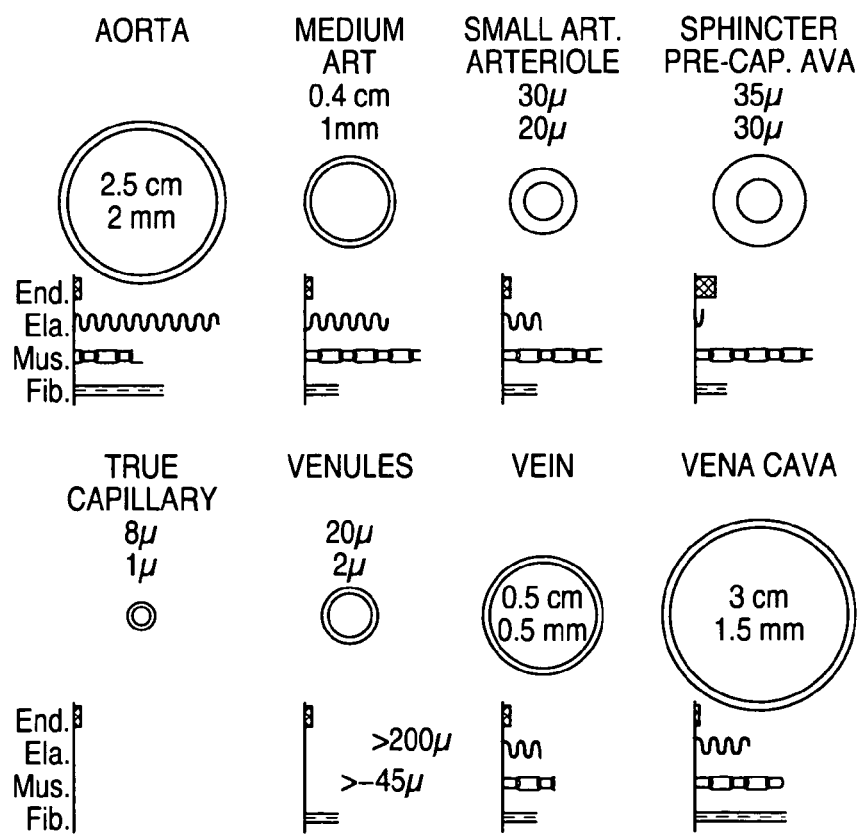
FIG. 5 shows cross-section sizes of various blood vessels.
Figure 6:
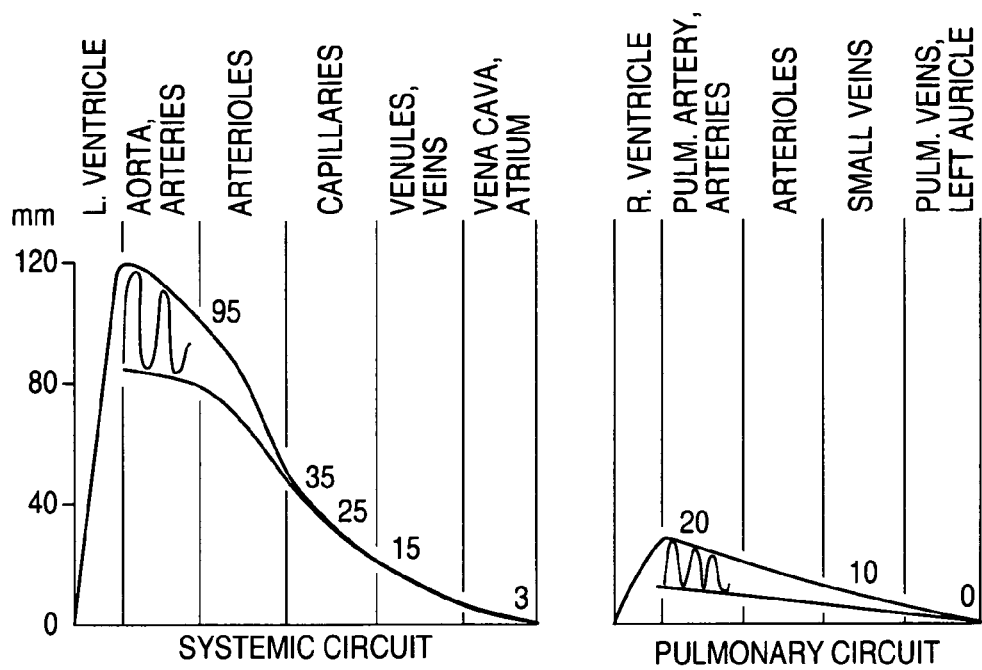
FIG. 6 gives the distribution of intravascular pressures.
Figure 7:
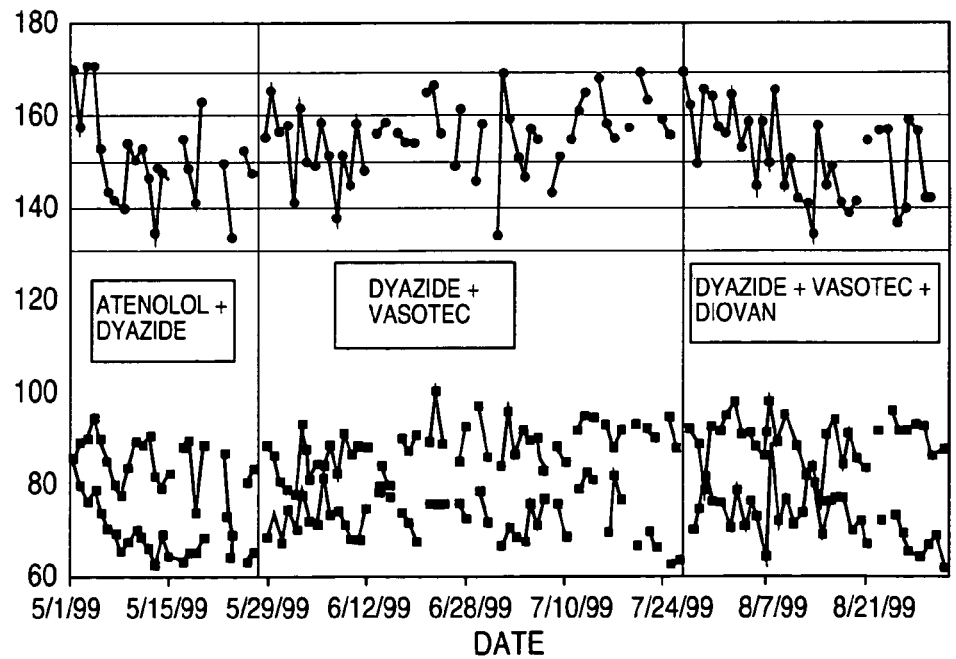
FIG. 7 gives the pulse rate and blood pressures of a 64-year-old patient in mornings during a four-month period while the patient's hypertension medications were being changed.
Figure 8:
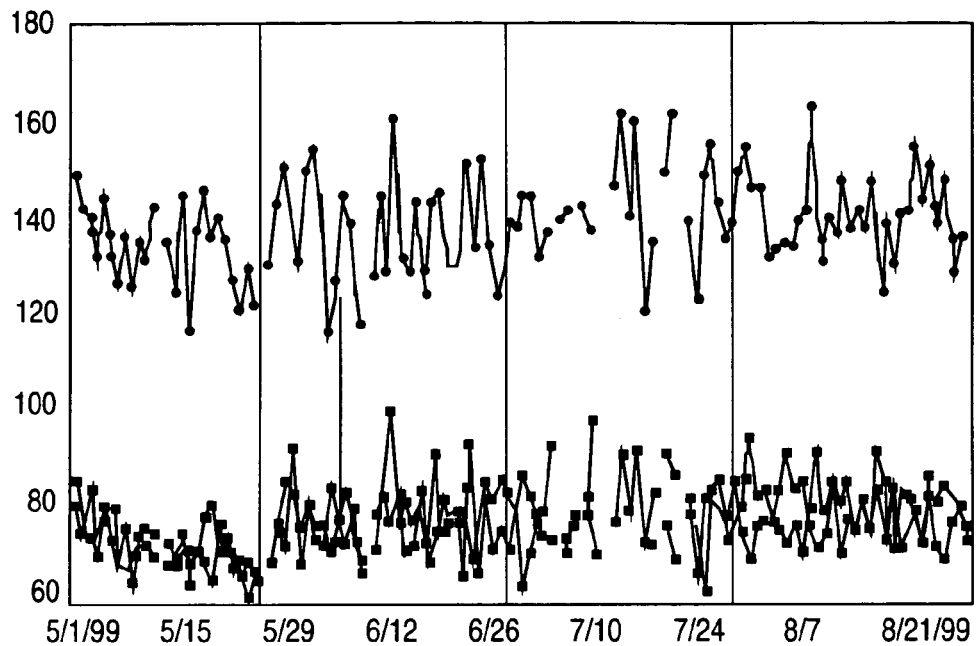
FIG. 8 shows blood pressure and pulse rate readings during evenings of the four-month period referred to with regard to FIG. 7.
Figure 9:
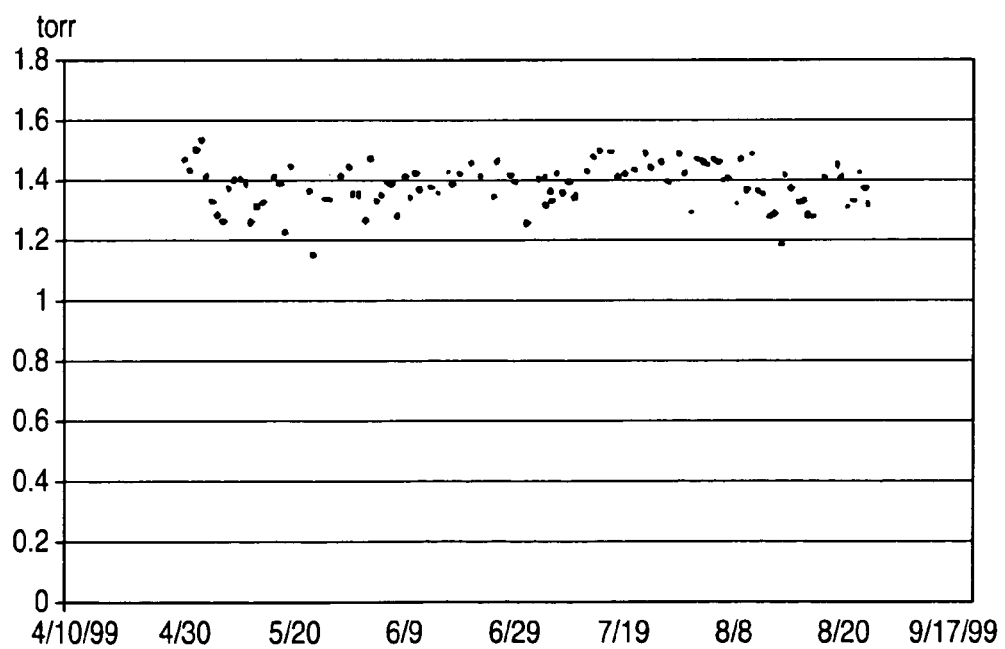
FIG. 9 shows measurement of AM normalized micro-peripheral resistance.
Figure 10:
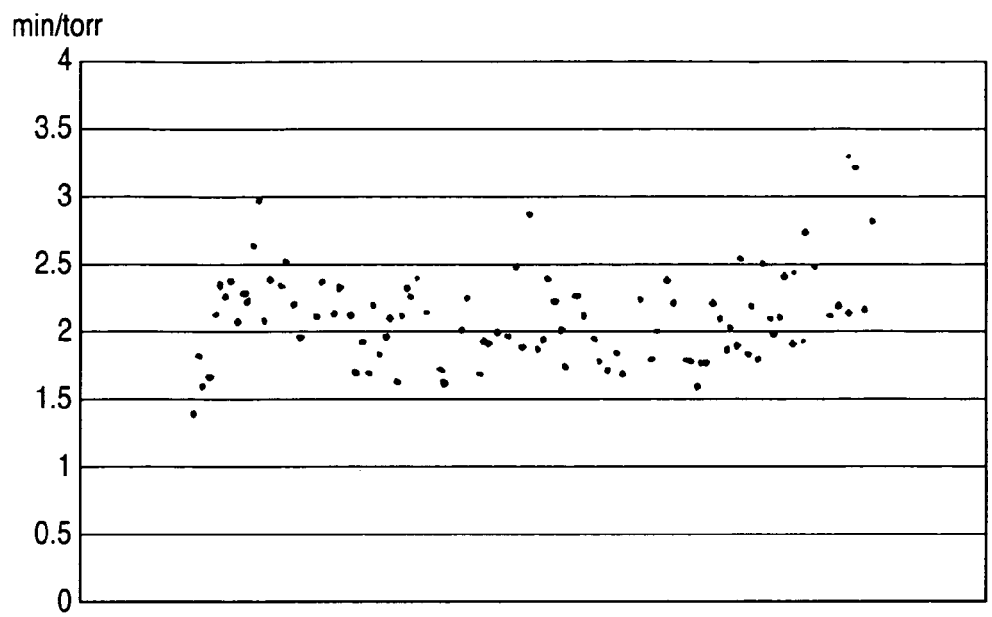
FIG. 10 shows AM normalized arterial distensibility.
Figure 11:
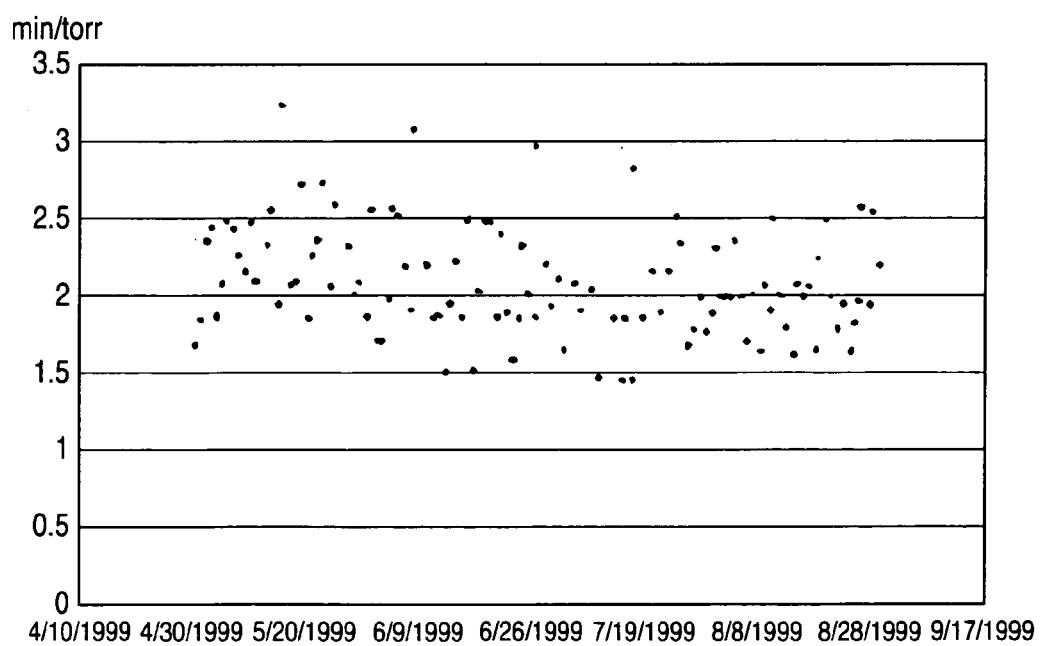
FIG. 11 shows PM normalized micro-peripheral resistance.
Figure 12:
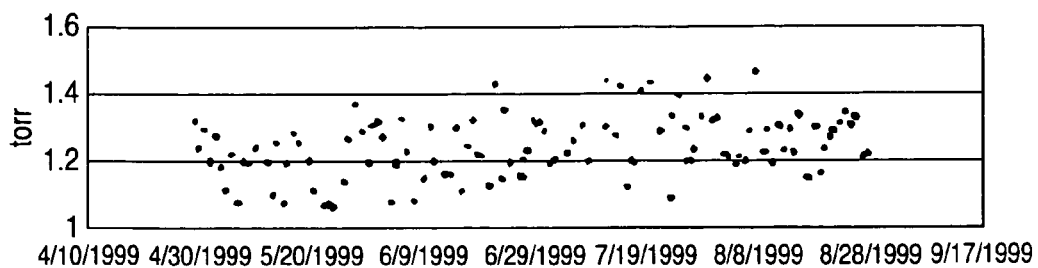
FIG. 12 shows the Range of Systemic Arterial Pressures vs age.

As shown in FIG. 4, the time course of the pressure in the arterial tree changes slightly from the aorta plot 402 to the plot 404 of the outlying main arteries. The change in the time course has been ascribed to reflections from branching points, selective damping of higher frequency components, and dispersion due to frequency-dependent phase velocities. The rise time of the pulse is so much shorter than the decay time that in the lowest approximation it can be assumed that the stroke volume is injected instantaneously into the arterial tree. After injection, the blood volume V in the arterial tree is assumed to decrease at a rate proportional to the pressure in the tree, since it is this pressure that causes the blood to flow from the tree.

$$dV/dt = -P/Z \quad [2]$$

Here, Z denotes the resistance to flow presented by the microvasculature fed by the arteries. This gives an exponential pressure decline—a smoothed version of the arterial pressure decline seen in FIG. 4. At any instant, the pressure P is equal to the pressure that exists just before the stroke volume is injected into the tree—i.e. the diastolic pressure $P_D$, plus the pressure $\delta P$ of eq. [1]

$$P = P_D + \delta P \quad [3]$$

Similarly, the instantaneous volume of the arterial tree is equal to the sum of the volume just before a stroke volume is injected, $V_D$, plus the sum of the volumes $\delta V_i$ of eq. [1]

$$V = V_D + \Sigma \delta V_i \quad [4]$$

On inserting [1] and [3] into [2]

$$d\delta P/dt = -(1/DZ)(P_D + \delta P) \quad [5]$$

where $$D = \Sigma D_i \quad [6]$$

the sum being over the body arteries. The general solution to equation [5] is $$\delta P = P_D + C \exp(-t/DZ) \quad [7]$$

The constant C can be evaluated at t=0 where it is known that by definition the increment in pressure is equal to the difference between the systolic pressure $P_S$ and the diastolic pressure $P_D$ $$\delta P(t=0) = P_S - P_D \quad [8]$$

Accordingly, $$C = P_S \quad [9]$$

and so $$P = P_D + \delta P = P_S \exp(-t/DZ) \quad [10]$$

If the pulse rate, f, is some number of pulses per minute, then the end of the period, t, occurs when t=1/f. At that time, the pressure must once again be the diastolic pressure $P_D$. Thus, the relationship can be shown as:

$$P_S = P_D \exp(1/DZf) \quad [11]$$

Since the arterial distensibility D, peripheral resistance Z, and pulse rate f, all enter into the exponent in this relationship, the ratio of systolic to diastolic pressure can depend sensitively on these parameters.

At t=0, the total change in volume from the diastolic volume (the volume just before injection of the stroke volume) must be equal to the stroke volume $V_S$. Equation [1] then shows (on using eq. [8]) that:

$$V_S = D(P_S - P_D) \quad [12]$$

The cardiac output <dV/dt> is the product of the pulse rate and the stroke volume. Then $$<dV/dt> = fD(P_S - P_D) \quad [13]$$

From [13] and [11]:

Arterial distensibility: $D = <dV/dt>[f(P_S - P_D)]^{-1} \quad [14]$

Peripheral resistance $Z = (P_S - P_D)[<dV/dt>\ln(P_S/P_D)]^{-1} \quad [15]$

Equations [14] and [15] show that:

$$D_N = D/<dV/dt> = [f(P_S - P_D)]^{-1} \quad [16]$$

$$R_N = Z<dV/dt> = (P_S - P_D)[\ln(P_S/P_D)]^{-1} \quad [17]$$

The left sides of [16] and [17] are respectively, normalized distensibility, $D_N$, and normalized peripheral resistance, $R_N$. As shown, these terms are expressible solely in terms of quantities routinely and easily measured in local medical offices and represent parameters which are normalized by cardiac output. The product of these values $DR=D_N R_N$, is independent of cardiac output. The significance and utility of eqs. [16] and [17] derives from records of their values in association with several medical conditions.

Figure 13:
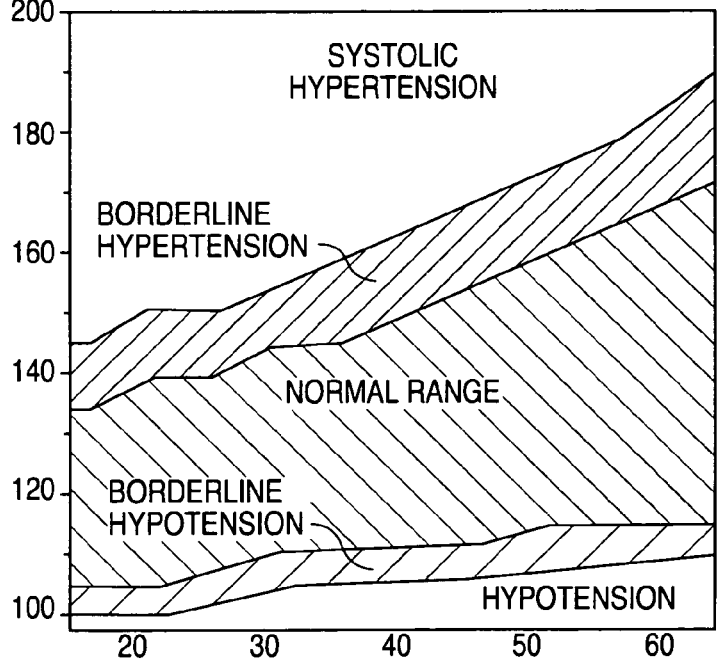
FIG. 13 shows Normal Micro-Peripheral Resistance Ranges where the upper limits correspond to borderline hypertension, and the lower limits to borderline hypotension.
Figure 13:
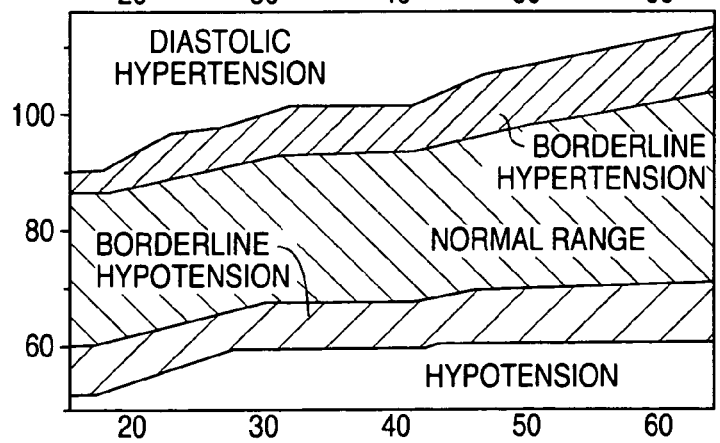
Figure 14:
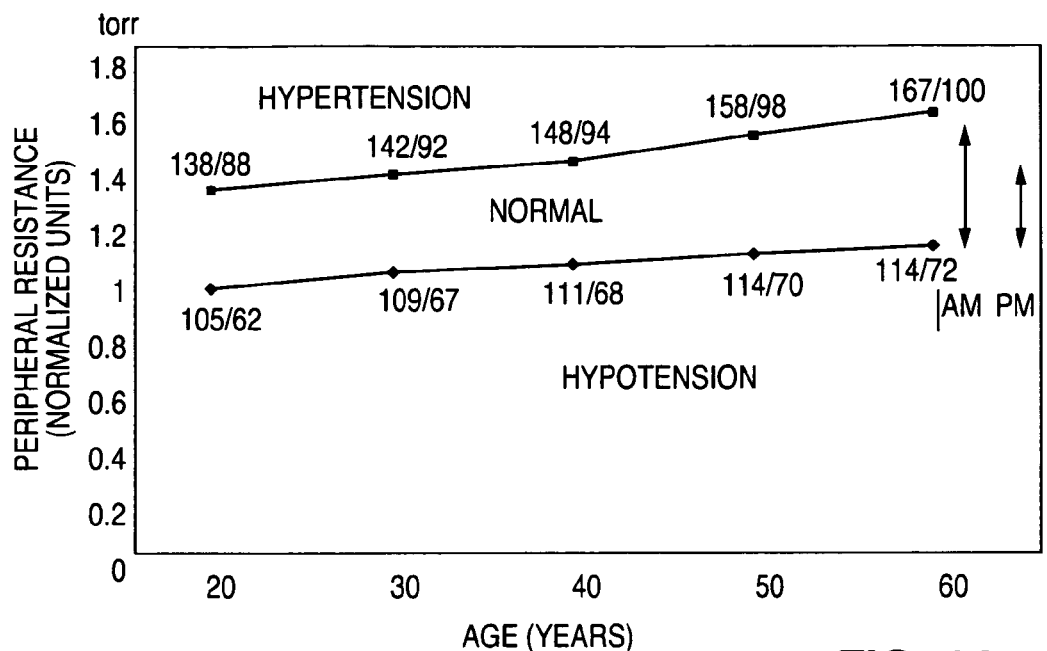
FIG. 14. shows normalized peripheral resistance vs. age.
Figure 15:
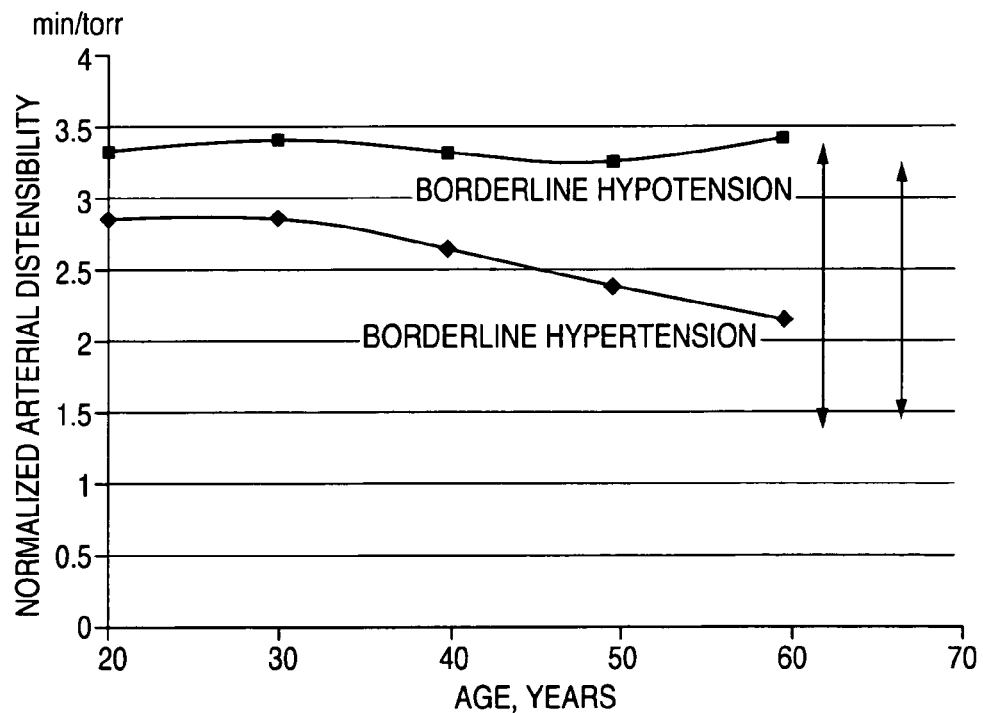
FIG. 15 shows the range of normalized arterial distensibility for a pulse rate of 70 per minute, where limits correspond to borderline hypertension (bottom) and borderline hypotension (top)
Figure 16:
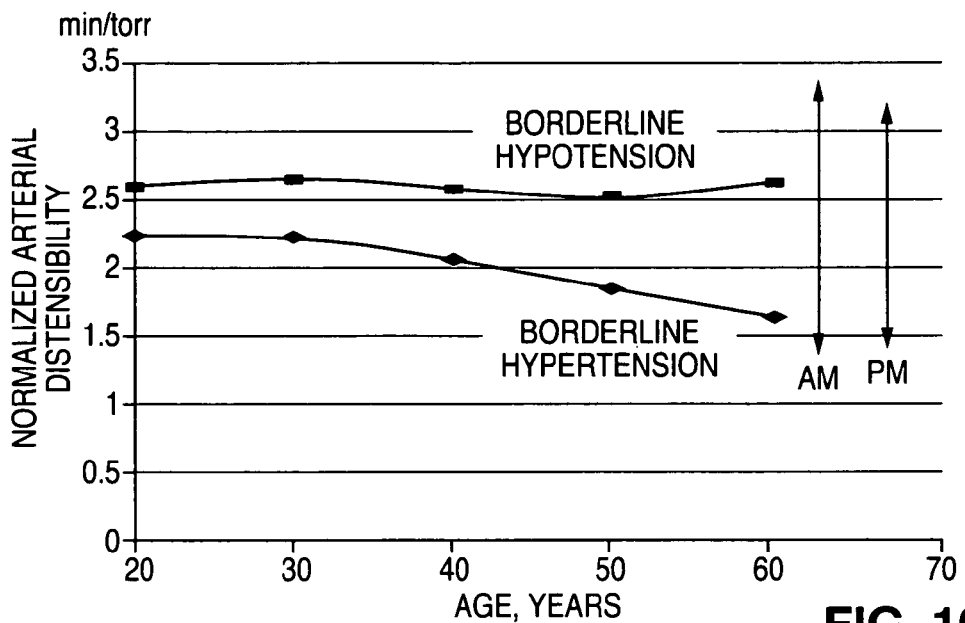
FIG. 16 shows the range of normalized arterial distensibility for a pulse rate of 90 per minute, where limits correspond to borderline hypertension (bottom) and borderline hypotension (top)

The normal reference values of blood pressures for typical subjects are shown in FIG. 13. If the values of diastolic pressure and systolic pressure at the boundaries of the normal range are taken, then the corresponding normal values for $D_N$ and $R_N$ are as shown in FIGS. 14–16.

The $R_N$ is independent of pulse rate, while the $D_N$ depends on pulse rate. FIG. 15 shows the values of $D_N$ for a pulse rate of 70 per minute and FIG. 16 shows the values for $D_N$ for a pulse rate of 90 per minute. Also shown on each plot are two double-ended arrows, indicating the range of values for the morning and evening readings for a subject.

Figure 17:
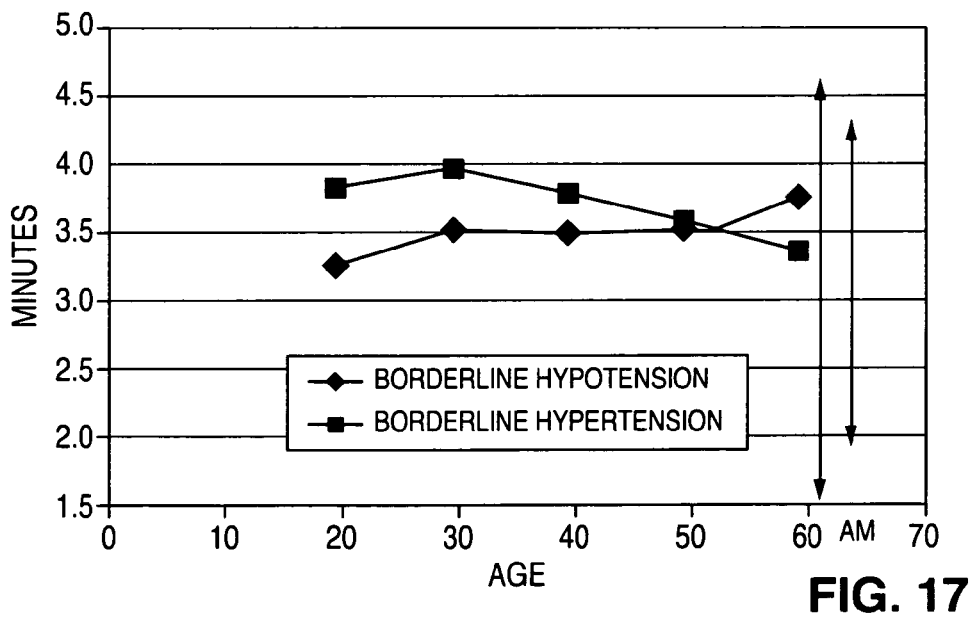
FIG. 17 shows limits of the product of normalized distensibility and normalized peripheral resistance for 70 beats/minute.

FIG. 17 shows that the normal values of $D_N$ and $R_N$ fall within in a narrow range. This is in contrast to the values obtained on one hypertensive subject over the time period of several months which were found to vary widely about the reference values.

Figure 1:
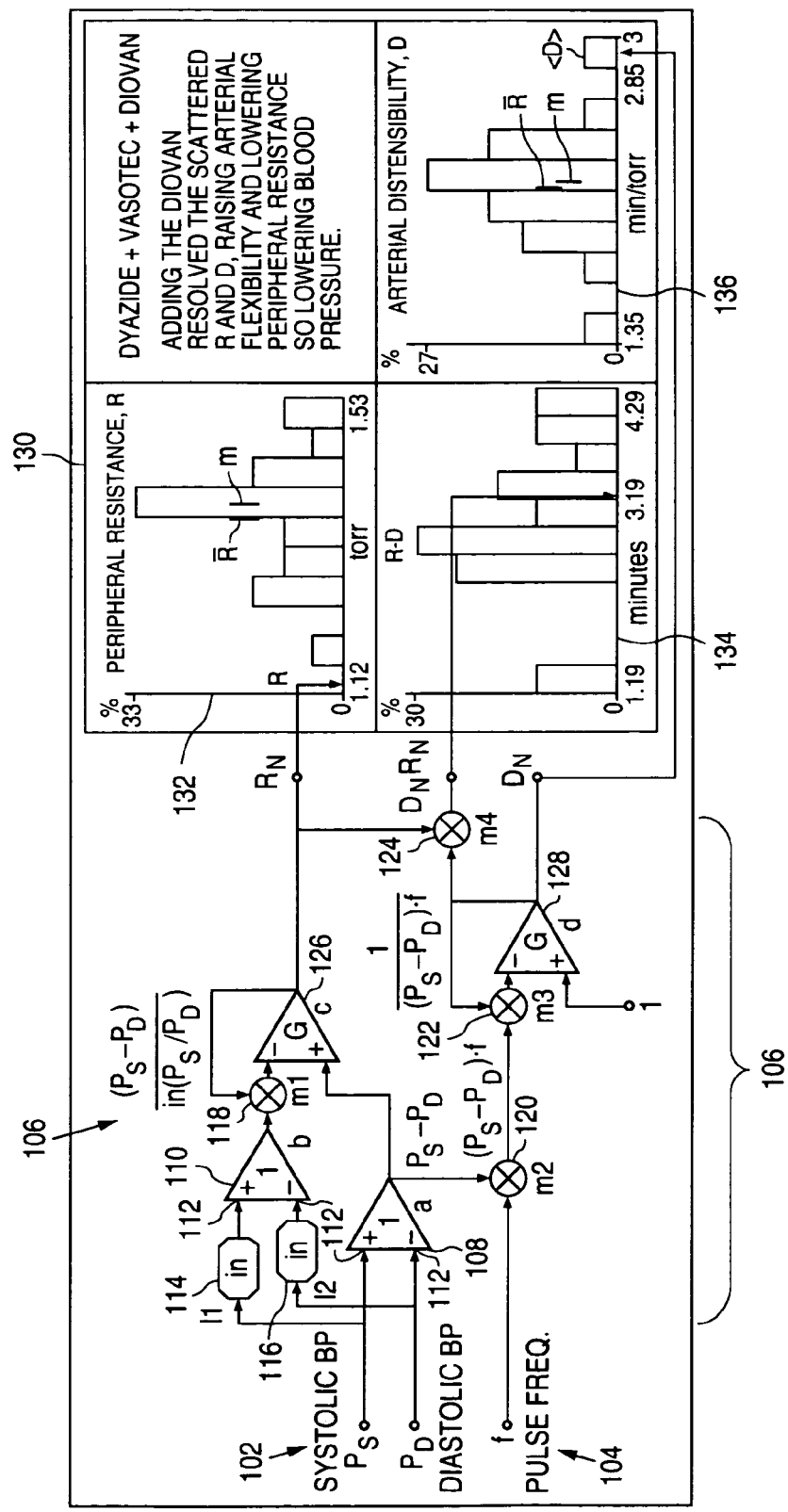
FIG. 1 is a simplified illustration of a block flow diagram illustrating an embodiment of the present invention.

FIG. 1 shows the entry and processing of blood pressure numeric data 102 and pulse rate numeric data 104 into a computer 106. A wide variety of analog or digital computers may be used, such as hand-held, laptop, or desktop computers, the selection turning mostly on clinical convenience. The blood pressure data 102 can be gathered from a standard inflatable cuff and sphygmomanometer. The pulse rate data 104 can be gathered by manual timing of the pulse or from automatic equipment that can deliver the data electronically to computer 106.

The systolic and diastolic pressures, expressed numerically in a consistent set of units, for example, torr, are entered into computer 106. The difference between these pressure numbers is produced and then divided by the natural logarithm of their ratio. The result is the $R_N$.

In the embodiment shown in FIG. 1, unity gain amplifiers 108 and 110, produce differences of input numbers, indicated by arrowheads 112. Conventional logarithmic elements 114 and 116 produce natural logarithms of their input numbers. Conventional multipliers, 118, 120, 122, and 124, produce the products of two input numbers each. Amplifiers 126 and 128, each of gain G>>1, produce division of input numbers. The output of amplifier 126, Co for instance, is $Co=G\cdot(P_S-P_D)-G\cdot[\ln(P_S)-\ln(P_D)]\cdot Co$. Solving for Co gives $Co=G\cdot(P_S-P_D)/\{1+G\cdot[\ln(P_S)-\ln(P_D)]\}$ which, because G>>1 gives $Co \approx (P_S-P_D)/[\ln(P_S)-\ln(P_D)]=(P_S-P_D)/\ln(P_S/P_D)=R_N$, normalized peripheral resistance. In like manner, the output of amplifier 128 is $Do=1/[(P_S-P_D)\cdot f]=D_N$, normalized arterial distensibility, where f is in units of beats per minute, for example. These two outputs and their product $D_N R_N$ are applied to a standard display device 130, which includes analog to digital converters producing called out numbers on the appropriate abscissa, as indicated in FIG. 1.

The three histograms 132, 134 and 136 shown in FIG. 1 display statistical data taken from a collection of similar individuals. For example, the statistical data can be taken from the first month of the patient's examinations (21 exams during this period), the idea being to substitute the ensemble average by a time average, the ergotic hypothesis of statistical mechanics.

The utility of these normalized measures is given in an example of a hypertensive scleroderma patient for whom values for blood pressure readings, heart rate, $D_N$, and $R_N$ obtained over a four month period are displayed in FIGS. 7–12. In this patient, before adequate treatment, the value for DR was below normal, the value for $R_N$ was within normal limits and the value for $D_N$ was below normal. The patient's range of these values is displayed with reference to normal values in FIGS. 14–15. It can be inferred from these values that his hypertension was due to a decrease in normalized artery distensibility rather than to scleroderma-related increase in normalized peripheral resistance. These results would guide a clinician to select those drugs which inhibit vasoconstriction rather than those which address increased cardiac output such as beta-blockers and diuretics. Routine and automatic recording of the parameters, thus building a statistical database, would be a useful diagnostic adjunct to individual blood pressure and pulse rate readings thereby improving monitoring for therapeutic efficacy.

Figure 18:
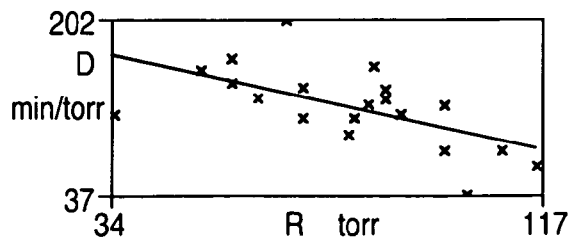
FIG. 18 shows a correlation between distensibility and peripheral resistance.

FIG. 18 shows the correlation between $D_N$ and $R_N$ in the first 24 exams. Unlike these data, the single points indicated by the arrows in the Peripheral Resistance and Arterial Resistance histograms of FIG. 1 were taken near the end of the four-month examination period where hypertension was under control. Arterial Distensibility, $D_N$, increased and Peripheral Resistance, $R_N$, decreased because of the correlation between them.

Although the present invention is described with reference to the presently preferred embodiments, it is understood that the invention as defined by the claims is not limited to these described embodiments. Various other changes and modifications to the invention will be recognized by those skilled in this art and will still fall within the scope and spirit of the invention, as defined by the accompanying claims.

What is claimed is:

1. A medical diagnostic method using systolic and diastolic blood pressures, and pulse frequency of a patient comprising:
   computing a normalized arterial distensibility value and a normalized peripheral resistance value using at least in part said systolic and diastolic pressure and pulse frequency;
   computing the product of said normalized arterial distensibility value and said normalized peripheral resistance value to generate a first product value; and
   comparing said first product value to a stored distribution of normalized diastolic distensibility and a normalized peripheral resistance values for comparable individuals to determine if said first product value is equivalent to a value determined to indicate an abnormal condition.

2. The method of claim 1, further comprising prescribing a medication from a list of medications that are indicated in said abnormal condition.

3. The method of claim 1, wherein said computing said normalized diastolic distensibility and said normalized peripheral resistance comprises measuring, with standard or automatic equipment, the systolic and diastolic blood pressures, and pulse frequency of a resting patient.

4. The method of claim 1, further comprising displaying said normalized arterial distensibility value and said normalized peripheral resistance value and the first product value on a display device.

5. The method of claim 1, wherein said blood pressures are determined using a standard inflatable cuff and sphygmomanometer and said pulse frequency is determined by manual timing of the pulse.

6. The method of claim 1, wherein said computing said normalized peripheral resistance value comprises taking the difference between the systolic and diastolic blood pressures and dividing the result by the natural logarithm of their ratio.

7. The method of claim 1, wherein said computing said normalized arterial distensiblity value comprises dividing the pulse period, reciprocal of pulse frequency, by the difference between the systolic and diastolic blood pressures.

8. The method of claim 1, further comprising determining a type of therapeutic intervention for the patient based on the normalized arterial distensibility value, the normalized peripheral resistance value, and the first product value.

9. The method of claim 8, wherein the type of therapeutic intervention comprises determining the type of drugs given to the patient.

10. The method of claim 1, further comprising determining effectiveness of a therapeutic intervention for the patient based on the normalized arterial distensibility value, the normalized peripheral resistance value, and the first product value.

11. A medical diagnostic system comprising:
a device for computing a normalized arterial distensibility value and a normalized peripheral resistance value using systolic and diastolic blood pressures, and pulse frequency of a patient;
a device for computing the product of said normalized arterial distensibility value and said normalized peripheral resistance value to generate a first product value; and
a device for comparing said first product value to a stored distribution of normalized arterial distensibility and a normalized peripheral resistance values for comparable individuals to determine if said first product value is equivalent to a value determined to indicate an abnormal condition.

12. The system of claim 11, further comprising means for measuring with standard or automatic equipment the systolic and diastolic blood pressures, and pulse frequency of a resting patient.

13. The system of claim 12, wherein said means for measuring comprises a standard inflatable cuff and sphygmomanometer.

14. The system of claim 13, further comprising a displaying device for displaying said normalized arterial distensibility value and said normalized peripheral resistance value and the first product value.

15. The system of claim 11, wherein device for computing the product of said normalized peripheral resistance value comprises a means for taking the difference between the systolic and diastolic blood pressures and dividing the result by the natural logarithm of their ratio.

16. The system of claim 11, wherein said device for computing said normalized arterial distensiblity value comprises a means for dividing the pulse period, reciprocal of pulse frequency, by the difference between the systolic and diastolic blood pressures.

17. A medical diagnostic system comprising:
a combination of components for determining biological data including the systolic blood pressure, the diastolic blood pressure, and the pulse frequency of a patient; and
a microprocessor configured to receive said biological data and including of performing the following:
compute a normalized arterial distensibility value and a normalized peripheral resistance value from said biological data;
compute the product of said normalized arterial distensibility value and said normalized peripheral resistance value to generate a first product value; and
compare said first product value to a stored distribution of normalized arterial distensibility and a normalized peripheral resistance values for comparable individuals to determine if said first product value is equivalent to a value determined to indicate an abnormal condition.

18. The system of claim 17, further comprising a display device to display said normalized arterial distensibility value and said normalized peripheral resistance value and the first product value together with distributions of such values from a population of comparable individuals.

19. The system of claim 17, wherein said components comprise a standard inflatable cuff and sphygmomanometer and a means for determination of said pulse rate.

20. The system of claim 17, wherein to compute said normalized peripheral resistance value comprises taking the difference between the systolic and diastolic blood pressures and dividing the result by the natural logarithm of their ratio.

21. The system of claim 17, wherein to compute said normalized arterial distensiblity value comprises dividing the pulse period, reciprocal of pulse frequency, by the difference between the systolic and diastolic blood pressures.

22. The system of claim 17, wherein the normalized arterial distensibility value, the normalized peripheral resistance value, and the first product value are used to determine a type of therapeutic intervention for the patient.

23. The system of claim 22, wherein the type of therapeutic intervention comprises the type of drugs given to the patient.

24. The system of claim 17, wherein the normalized diastolic distensibility value, the normalized peripheral resistance value, and the first product value are used to determine effectiveness of a therapeutic intervention for the patient.

* * * * *